US009486276B2

(12) United States Patent
Rios et al.

(10) Patent No.: US 9,486,276 B2
(45) Date of Patent: Nov. 8, 2016

(54) DEVICES AND METHODS FOR FISTULA FORMATION

(71) Applicant: TVA Medical, Inc., Austin, TX (US)

(72) Inventors: Jesus M. Rios, Alvin, TX (US);
William E. Cohn, Bellaire, TX (US);
Dheeraj K. Rajan, Toronto (CA);
Adam L. Berman, Austin, TX (US);
Dana R. Mester, Austin, TX (US);
Damian A. Jelich, Austin, TX (US)

(73) Assignee: TVA Medical, Inc., Austin, TX (US)

( * ) Notice: Subject to any disclaimer, the term of this patent is extended or adjusted under 35 U.S.C. 154(b) by 154 days.

(21) Appl. No.: 14/052,477

(22) Filed: Oct. 11, 2013

(65) Prior Publication Data

US 2014/0107642 A1    Apr. 17, 2014

Related U.S. Application Data

(60) Provisional application No. 61/712,704, filed on Oct. 11, 2012, provisional application No. 61/785,548, filed on Mar. 14, 2013.

(51) Int. Cl.
| | |
|---|---|
| *A61B 18/14* | (2006.01) |
| *A61B 17/32* | (2006.01) |
| *A61M 25/01* | (2006.01) |
| *A61M 1/36* | (2006.01) |

(Continued)

(52) U.S. Cl.
CPC ..... *A61B 18/148* (2013.01); *A61B 17/320016* (2013.01); *A61B 17/3478* (2013.01); *A61B 18/1492* (2013.01); *A61M 1/3655* (2013.01); *A61M 25/01* (2013.01); *A61B 2017/00252* (2013.01); *A61B 2017/22077* (2013.01); *A61B 2018/00202* (2013.01); *A61B 2018/00404* (2013.01); *A61B 2018/00577* (2013.01)

(58) Field of Classification Search
CPC .......... A61B 2017/1139; A61B 17/11; A61B 2017/1107
See application file for complete search history.

(56) References Cited

U.S. PATENT DOCUMENTS 5,830,222 A    11/1998  Makower
5,830,224 A *  11/1998  Cohn et al. .................... 606/167

(Continued)

FOREIGN PATENT DOCUMENTS

CN    101730557 A    6/2010
EP      0889705 A1    1/1999

(Continued)

OTHER PUBLICATIONS

International Preliminary Report on Patentability received for PCT Patent Application No. PCT/US2011/061026, mailed on May 30, 2013, 8 pages.

(Continued)

*Primary Examiner* — Jocelyn D Ram
(74) *Attorney, Agent, or Firm* — Cooley LLP (57) ABSTRACT

Described here are devices and methods for forming a fistula between two vessels. In some instances, the fistula may be formed between a proximal ulnar artery and a deep ulnar vein. The fistula may be formed using an electrode, and may be formed with a first catheter placed in a first blood vessel and a second catheter placed in a second blood vessel. In some instances, access to the proximal ulnar artery may be achieved through a brachial artery, and access to the deep ulnar vein may be achieved through a brachial vein.

23 Claims, 7 Drawing Sheets

(51) Int. Cl.
*A61B 17/34* (2006.01)
*A61B 17/00* (2006.01)
*A61B 17/22* (2006.01)
*A61B 18/00* (2006.01)

(56) References Cited

U.S. PATENT DOCUMENTS

| | | |
|---|---|---|
| 6,004,330 A | 12/1999 | Middleman et al. |
| 6,032,677 A | 3/2000 | Blechman et al. |
| 6,099,542 A | 8/2000 | Cohn et al. |
| 6,217,575 B1 | 4/2001 | DeVore et al. |
| 6,256,525 B1 | 7/2001 | Yang et al. |
| 6,287,306 B1 | 9/2001 | Kroll et al. |
| 6,302,875 B1 | 10/2001 | Makower et al. |
| 6,357,447 B1 | 3/2002 | Swanson et al. |
| 6,379,353 B1 | 4/2002 | Nichols |
| 6,400,976 B1 | 6/2002 | Champeau |
| 6,461,356 B1 | 10/2002 | Patterson |
| 6,464,665 B1 | 10/2002 | Heuser |
| 6,475,214 B1 | 11/2002 | Moaddeb |
| 6,527,769 B2 | 3/2003 | Langberg et al. |
| 6,542,766 B2 | 4/2003 | Hall et al. |
| 6,569,162 B2 | 5/2003 | He |
| 6,656,173 B1 | 12/2003 | Palermo |
| 6,663,625 B1 | 12/2003 | Ormsby et al. |
| 6,669,709 B1 | 12/2003 | Cohn et al. |
| 6,676,657 B2 | 1/2004 | Wood |
| 6,719,756 B1 | 4/2004 | Muntermann |
| 6,726,697 B2 * | 4/2004 | Nicholas ............... A61B 17/11 227/179.1 |
| 6,780,181 B2 | 8/2004 | Kroll et al. |
| 6,849,073 B2 | 2/2005 | Hoey et al. |
| 6,855,143 B2 | 2/2005 | Davison et al. |
| 6,911,026 B1 | 6/2005 | Hall et al. |
| 6,932,814 B2 | 8/2005 | Wood |
| 6,960,209 B2 | 11/2005 | Clague et al. |
| 6,971,983 B1 | 12/2005 | Cancio |
| 7,060,063 B2 | 6/2006 | Marion et al. |
| 7,155,293 B2 | 12/2006 | Westlund et al. |
| 7,189,231 B2 | 3/2007 | Clague et al. |
| 7,231,260 B2 | 6/2007 | Wallace et al. |
| 7,288,075 B2 | 10/2007 | Parihar et al. |
| 7,306,598 B2 | 12/2007 | Truckai et al. |
| 7,341,063 B2 | 3/2008 | Garbibaldi et al. |
| 7,387,636 B2 * | 6/2008 | Cohn et al. ............... 606/167 |
| 7,628,768 B2 | 12/2009 | Faul et al. |
| 7,702,387 B2 | 4/2010 | Stevenson et al. |
| 7,744,596 B2 | 6/2010 | Young et al. |
| 7,811,281 B1 | 10/2010 | Rentrop |
| 7,828,814 B2 | 11/2010 | Brenneman et al. |
| 7,846,172 B2 | 12/2010 | Makower |
| 7,857,809 B2 | 12/2010 | Drysen |
| 7,881,797 B2 | 2/2011 | Griffin et al. |
| 7,955,326 B2 | 6/2011 | Paul et al. |
| 7,967,769 B2 | 6/2011 | Faul et al. |
| 8,010,208 B2 | 8/2011 | Nimer et al. |
| 8,048,016 B2 | 11/2011 | Faul et al. |
| 8,052,680 B2 | 11/2011 | Hassett et al. |
| 8,062,321 B2 | 11/2011 | Heuser et al. |
| 8,075,555 B2 | 12/2011 | Truckai et al. |
| 8,088,171 B2 | 1/2012 | Brenneman |
| 8,100,899 B2 | 1/2012 | Doty et al. |
| 8,118,809 B2 | 2/2012 | Paul et al. |
| 8,135,467 B2 | 3/2012 | Markowitz et al. |
| 8,192,425 B2 | 6/2012 | Mirza et al. |
| 8,226,592 B2 | 7/2012 | Brenneman et al. |
| 8,231,618 B2 | 7/2012 | Viswanathan et al. |
| 8,236,014 B2 | 8/2012 | Brenneman et al. |
| 8,273,095 B2 | 9/2012 | Brenneman et al. |
| 8,382,697 B2 * | 2/2013 | Brenneman et al. ............... 604/9 |
| 8,409,196 B2 | 4/2013 | Durgin et al. |
| 8,414,572 B2 | 4/2013 | Davison et al. |
| 8,439,909 B2 | 5/2013 | Wang et al. |
| 8,486,064 B2 | 7/2013 | Van Wyk et al. |
| 8,649,879 B2 | 2/2014 | Digiore et al. |
| 8,700,179 B2 | 4/2014 | Pianca et al. |
| 8,790,341 B2 | 7/2014 | Pappone et al. |
| 9,017,323 B2 * | 4/2015 | Miller et al. ............... 606/41 |
| 9,039,702 B2 * | 5/2015 | Miller et al. ............... 606/41 |
| 2001/0029384 A1 * | 10/2001 | Nicholas ............... 606/153 |
| 2004/0059211 A1 * | 3/2004 | Patel et al. ............... 600/325 |
| 2004/0236360 A1 * | 11/2004 | Cohn et al. ............... 606/167 |
| 2005/0033401 A1 | 2/2005 | Cunniffe et al. |
| 2006/0079897 A1 | 4/2006 | Harrison et al. |
| 2006/0111704 A1 | 5/2006 | Brenneman et al. |
| 2007/0173878 A1 | 7/2007 | Heuser |
| 2007/0203515 A1 * | 8/2007 | Heuser et al. ............... 606/184 |
| 2008/0021532 A1 | 1/2008 | Kveen et al. |
| 2008/0065019 A1 * | 3/2008 | Heuser et al. ............... 604/164.03 |
| 2008/0091192 A1 | 4/2008 | Paul et al. |
| 2008/0119879 A1 * | 5/2008 | Brenneman et al. ............... 606/153 |
| 2008/0171944 A1 * | 7/2008 | Brenneman et al. ............... 600/509 |
| 2009/0076324 A1 | 3/2009 | Takayama et al. |
| 2009/0112119 A1 | 4/2009 | Kim |
| 2009/0275876 A1 | 11/2009 | Brenneman et al. |
| 2009/0318849 A1 | 12/2009 | Hobbs et al. |
| 2010/0004623 A1 | 1/2010 | Hamilton, Jr. et al. |
| 2010/0010488 A1 | 1/2010 | Kassab et al. |
| 2010/0130835 A1 | 5/2010 | Brenneman et al. |
| 2010/0204691 A1 | 8/2010 | Bencini |
| 2010/0222664 A1 | 9/2010 | Lemon et al. |
| 2010/0256616 A1 | 10/2010 | Katoh et al. |
| 2010/0292685 A1 | 11/2010 | Katoh et al. |
| 2011/0015657 A1 | 1/2011 | Brenneman et al. |
| 2011/0112427 A1 | 5/2011 | Phillips et al. |
| 2011/0118735 A1 | 5/2011 | Abou-Marie et al. |
| 2011/0201990 A1 | 8/2011 | Franano |
| 2011/0213309 A1 * | 9/2011 | Young ............... A61B 17/0057 604/175 |
| 2011/0270149 A1 | 11/2011 | Faul et al. |
| 2011/0288392 A1 | 11/2011 | De La Rama et al. |
| 2011/0288544 A1 | 11/2011 | Verin et al. |
| 2012/0010556 A1 | 1/2012 | Faul et al. |
| 2012/0035539 A1 | 2/2012 | Tegg |
| 2012/0059398 A1 | 3/2012 | Pate et al. |
| 2012/0089123 A1 | 4/2012 | Organ et al. |
| 2012/0101423 A1 | 4/2012 | Brenneman |
| 2012/0116354 A1 | 5/2012 | Heuser |
| 2012/0157992 A1 | 6/2012 | Smith et al. |
| 2012/0239021 A1 | 9/2012 | Doty et al. |
| 2012/0281330 A1 | 11/2012 | Abbott et al. |
| 2012/0302935 A1 * | 11/2012 | Miller et al. ............... 604/8 |
| 2013/0056876 A1 | 3/2013 | Harvey et al. |
| 2013/0110105 A1 | 5/2013 | Vankov |
| 2013/0172881 A1 | 7/2013 | Hill et al. |
| 2013/0190754 A1 | 7/2013 | Paul et al. |
| 2013/0226170 A1 | 8/2013 | Seddon et al. |
| 2013/0282000 A1 | 10/2013 | Parsonage |
| 2014/0094791 A1 | 4/2014 | Hull et al. |
| 2014/0100557 A1 | 4/2014 | Bohner et al. |
| 2014/0107642 A1 | 4/2014 | Rios et al. |
| 2014/0166098 A1 | 6/2014 | Kian et al. |
| 2014/0276335 A1 * | 9/2014 | Pate ............... 604/8 |
| 2015/0080886 A1 * | 3/2015 | Miller et al. ............... 606/41 |
| 2015/0258308 A1 | 9/2015 | Pate |
| 2015/0313668 A1 | 11/2015 | Miller et al. |

FOREIGN PATENT DOCUMENTS

| | | |
|---|---|---|
| JP | 11-512640 A | 11/1999 |
| JP | 2004-501720 A | 1/2004 |
| JP | 3493464 B2 | 2/2004 |
| RU | 2168951 C1 * | 6/2001 |
| WO | 97/33522 A1 | 9/1997 |
| WO | 02/02163 A2 | 1/2002 |
| WO | 2012/068273 A1 | 5/2012 |

OTHER PUBLICATIONS

International Search Report and Written Opinion received for PCT Patent Application No. PCT/US2011/061026, mailed on Feb. 23, 2012, 8 pages.

(56) References Cited

OTHER PUBLICATIONS

International Search Report & Written Opinion received for PCT Patent Application No. PCT/US2013/064657, mailed on Jan. 10, 2014, 9 pages.
Office Action Received for Australian Patent Application No. 2011328926, issued on Jun. 2, 2014, 4 pages.
Non Final Office Action received for U.S. Appl. No. 13/298,169, mailed on Aug. 8, 2014, 15 pages.
International Search Report and Written Opinion received for PCT Patent Application No. PCT/US2014/029731, mailed on Aug. 22, 2014, 12 pages.
Notice of Allowance received for U.S. Appl. No. 13/298,169, mailed on Dec. 31, 2014, 10 pages.
Notice of Allowance received for U.S. Appl. No. 13/298,169, mailed on Mar. 11, 2015, 4 pages.
Notice of Allowance received for U.S. Appl. No. 14/550,747, mailed on Jan. 23, 2015, 3 pages.
Notice of Acceptance Received for Australian Patent Application No. 2011328926, mailed on Jun. 30, 2015, 2 pages.
Office Action Received for Chinese Patent Application No. 201180065285.1, mailed on Mar. 20, 2015, 7 pages (2 pages of English Translation and 5 pages of Official Copy).
Office Action received for Singapore Patent Application No. 201303477-2, mailed on Apr. 21, 2015, 8 pages.
Written Opinion received for Singapore Patent Application No. 201303477-2, mailed on Oct. 14, 2014, 10 pages.
International Preliminary Report on Patentability received for PCT Patent Application No. PCT/US2013/064657, mailed on Apr. 23, 2015, 8 pages.
International Search Report and Written Opinion received for PCT Patent Application No. PCT/US2015/020604, mailed on Jun. 17, 2015, 8 pages.
International Preliminary Report on Patentability received for PCT Patent Application No. PCT/US2014/029731, mailed on Sep. 24, 2015, 10 pages.
Office Action received for Japanese Patent Application No. 2013-539007, mailed on Sep. 8, 2015, 9 pages (5 pages of English Translation and 4 pages of Official Copy).
Banasik et al., "A Rare Variant Route of the Ulnar Artery Does Not Contraindicate the Creation of a Fistula in the Wrist of a Diabetic Patient with End-Stage Renal Disease", Postepy Hig Med Dosw (online), vol. 65, 2011, pp. 654-657.
Bharat et al., "A Novel Technique of Vascular Anastomosis to Prevent Juxta-Anastomotic Stenosis Following Arteriovenous Fistula Creation", Journal of Vascular Surgery, vol. 55, No. 1, Jan. 2012, pp. 274-280.
Bode et al., "Clinical Study Protocol for the arch Project Computational Modeling for Improvement of Outcome after Vascular Access Creation", J. Vasc. Access, vol. 12, No. 4, 2011, pp. 369-376.
Davidson et al., "Duplex Ultrasound Evaluation for Dialysis Access Selection and Maintenance: A Practical Guide", The Journal of Vascular Access, vol. 9, 2008, pp. 1-9.
Gracz et al., "Proximal Forearm Fistula for Maintenance Hemodialysis", Kidney International, vol. 11, 1977, pp. 71-75.
Jennings et al., "Primary Arteriovenous Fistula Inflow Proximalization for Patients at high Risk for Dialysis Access-Associated Ischemic Steal Syndrome", Journal of Vascular Surgery, 2011, 2 pages, abstract only.
Kinnaert et al., "Ulnar Arteriovenous Fistula for Maintenance Haemodialysis", The British Journal of Surgery, vol. 58, No. 9, Sep. 1971, pp. 641-643.
Morale et al., "Venae Comitantes as a Potential Vascular Resource to Create Native Arteriovenous Fistulae", J Vasc Access, vol. 12, No. 3, 2011, pp. 211-214.
Shenoy, Surendra, "Surgical Anatomy of Upper Arm: what is Needed for AVF Planning", The Journal of Vascular Access, vol. 10, 2009, pp. 223-232.
Vachharajani, Tushar J., "Atlas of Dialysis Vascular Access", Wake Forest University School of Medicine, 2010, 77 pages.
Whittaker et al., "Prevention Better than Cure. Avoiding Steal Syndrome with Proximal Radial or Ulnar Arteriovenous Fistulae", J Vasc Access, vol. 12, No. 4, 2011, pp. 318-320.
Non-Final Office Action received for U.S. Appl. No. 14/697,451, mailed on May 2, 2016, 12 pages.
Notice of Allowance received for Chinese Patent Application No. 201180065285.1, mailed on Nov. 26, 2015, 4 pages (2 pages of English Translation and 2 pages of Official Copy).
Notice of Allowance received for Mexican Patent Application No. MX/a/2013/005393, mailed on Oct. 30, 2015, 3 pages (2 pages of English Translation and 1 page of Official copy).

\* cited by examiner

DEVICES AND METHODS FOR FISTULA FORMATION

CROSS-REFERENCE TO RELATED APPLICATIONS

This application claims priority to U.S. Provisional Application Ser. No. 61/712,704, filed on Oct. 11, 2012 and titled "DEVICES AND METHODS FOR FISTULA FORMATION," and to U.S. Provisional Application Ser. No. 61/785,548, filed on Mar. 14, 2013 and titled "DEVICES AND METHODS FOR FISTULA FORMATION," the contents of which are hereby incorporated by reference in their entirety.

FIELD

The current invention relates to methods for forming a fistula between two blood vessels.

BACKGROUND

A fistula is generally a passageway formed between two internal organs. Forming a fistula between two blood vessels can have one or more beneficial functions. For example, the formation of a fistula between an artery and a vein may provide access to the vasculature for hemodialysis patients. Specifically, forming a fistula between an artery and a vein allows blood to flow quickly between the vessels while bypassing the capillaries. Needles, catheters, or other cannulas may then be inserted into the blood vessels near the fistula to draw blood from the circulatory system, pass it through a dialysis machine, and return it to the body. The quickened flow provided by the fistula may provide for effective hemodialysis. Generally, fistula formation requires the surgical dissection of a target vein, transecting and moving the vein for surgical anastomosis to the artery. These fistulas typically have a primary failure rate (failure before the patient receives dialysis) of about 30-60%, and take between 5 and 12 months before the fistula is usable for dialysis. It may be useful to find improved ways to form a fistula between two blood vessels.

BRIEF SUMMARY

In some variations, the methods described here comprise forming a first fistula between a proximal ulnar artery and a first deep ulnar vein. In some variations, the methods may further comprise endovascularly advancing a distal portion of a first catheter into the first deep ulnar vein. In some of these variations, the first catheter comprises a fistula-forming element, and forming the first fistula between the proximal ulnar artery and the first deep ulnar vein comprises forming the first fistula using the fistula-forming element. The fistula-forming element may be, for example, an electrode. In some of these variations, the methods further comprise moving the electrode away from the first catheter against a vessel wall of the deep ulnar vein, and wherein forming the first fistula between the proximal ulnar artery and the first deep ulnar vein comprises ablating the vessel wall of the deep ulnar vein and a vessel wall of the ulnar artery.

In some variations, the methods described here may further comprise advancing a distal portion of a second catheter into the ulnar artery. In some of these variations, the first and second catheters may each comprise one or more magnets and the method may further comprise aligning the first and second catheters using the one or more magnets of each of the first and second catheters. In some variations, the second catheter may comprise a fistula-forming element, and forming the first fistula between the proximal ulnar artery and the first deep ulnar vein comprises forming the first fistula using the fistula-forming element. The fistula-forming element may be, for example, an electrode. In some of these variations, the method may further comprise moving the electrode away from the second catheter against a vessel wall of the proximal ulnar artery, and forming the first fistula between the proximal ulnar artery and the first deep ulnar vein may comprise ablating the vessel wall of the proximal ulnar artery and a vessel wall of the first deep ulnar vein. In some variations, endovascularly advancing the distal portion of the second catheter into the proximal ulnar artery comprises endovascularly advancing the distal portion of the second catheter into the proximal ulnar artery from a brachial artery. In some of these variations, the method may further comprise creating an access site in the brachial artery and advancing the second catheter into the brachial artery through the access site.

In some variations, endovascularly advancing the distal portion of the first catheter into the first deep ulnar vein comprises endovascularly advancing the distal portion of the first catheter into the first deep ulnar vein from a median cubital vein. In some variations, the method may further comprise forming an access site in a basilic vein, introducing the distal portion of the first catheter into the basilic vein through the access site, and advancing the distal portion of the first catheter into the median cubital vein through the basilic vein.

In some variations, endovascularly advancing the distal portion of the first catheter into the first deep ulnar vein comprises endovascularly advancing the distal portion of the first catheter into the first deep ulnar vein from a median cephalic vein. In some variations, the method may further comprise forming an access site in a cephalic vein, introducing the distal portion of the first catheter into the cephalic vein through the access site, and advancing the distal portion of the first catheter into the median cephalic vein through the cephalic vein. In some variations, endovascularly advancing the distal portion of the first catheter into the first deep ulnar vein comprises endovascularly advancing the distal portion of the first catheter into the first deep ulnar vein from a first brachial vein. In some variations, the method may further comprise forming an access site in the first brachial vein, introducing the distal portion of the first catheter into the first brachial vein through the access site.

In some variations, the methods described here may comprise injecting a radiopaque dye into the proximal ulnar artery. Additionally or alternatively, the methods may comprise forming a second fistula between the proximal ulnar artery and a second deep ulnar vein. Additionally or alternatively, the methods may further comprise cannulating the cephalic vein and/or the basilic vein to provide dialysis access.

In other variations, the methods described here may comprise endovascularly advancing a distal portion of a first catheter through a portion of a basilic vein, a median cubital vein, and into a first deep ulnar vein, endovascularly advancing a distal portion of a second catheter through a portion of a brachial artery and into a ulnar artery, and forming a fistula between the first deep ulnar vein and the ulnar artery. In still variations, the methods described here may comprise endovascularly advancing a distal portion of a first catheter through a portion of a cephalic vein, a median cephalic vein, and into a first deep ulnar vein, endovascularly advancing a distal portion of a second catheter through a portion of a brachial artery and into a ulnar artery, and forming a fistula between the first deep ulnar vein and the ulnar artery. In yet other variations, the methods described here may comprise endovascularly advancing a distal portion of a first catheter through a portion of a first brachial vein and into a first deep ulnar vein, endovascularly advancing a distal portion of a second catheter through a portion of a brachial artery and into a ulnar artery, and forming a fistula between the first deep ulnar vein and the ulnar artery.

BRIEF DESCRIPTION

DETAILED DESCRIPTION

Generally described here are methods for forming one or more fistulas between blood vessels of the arm. The methods described here comprise forming a fistula between an ulnar artery and a deep ulnar vein, as will be described in detail below. The fistula may be formed using one or more catheters, which may be advanced endovascularly into an ulnar artery and/or a deep ulnar vein. In some variations a first catheter may be advanced into the ulnar artery, and a second catheter may be placed into a deep ulnar vein, and the first and second catheters may form a fistula therebetween. Access to the vascular sites may be achieved in a number of ways, such as will be described in more detail below. Accordingly, it may be helpful to briefly describe the anatomy of the vasculature of the arm.

Figure 1:
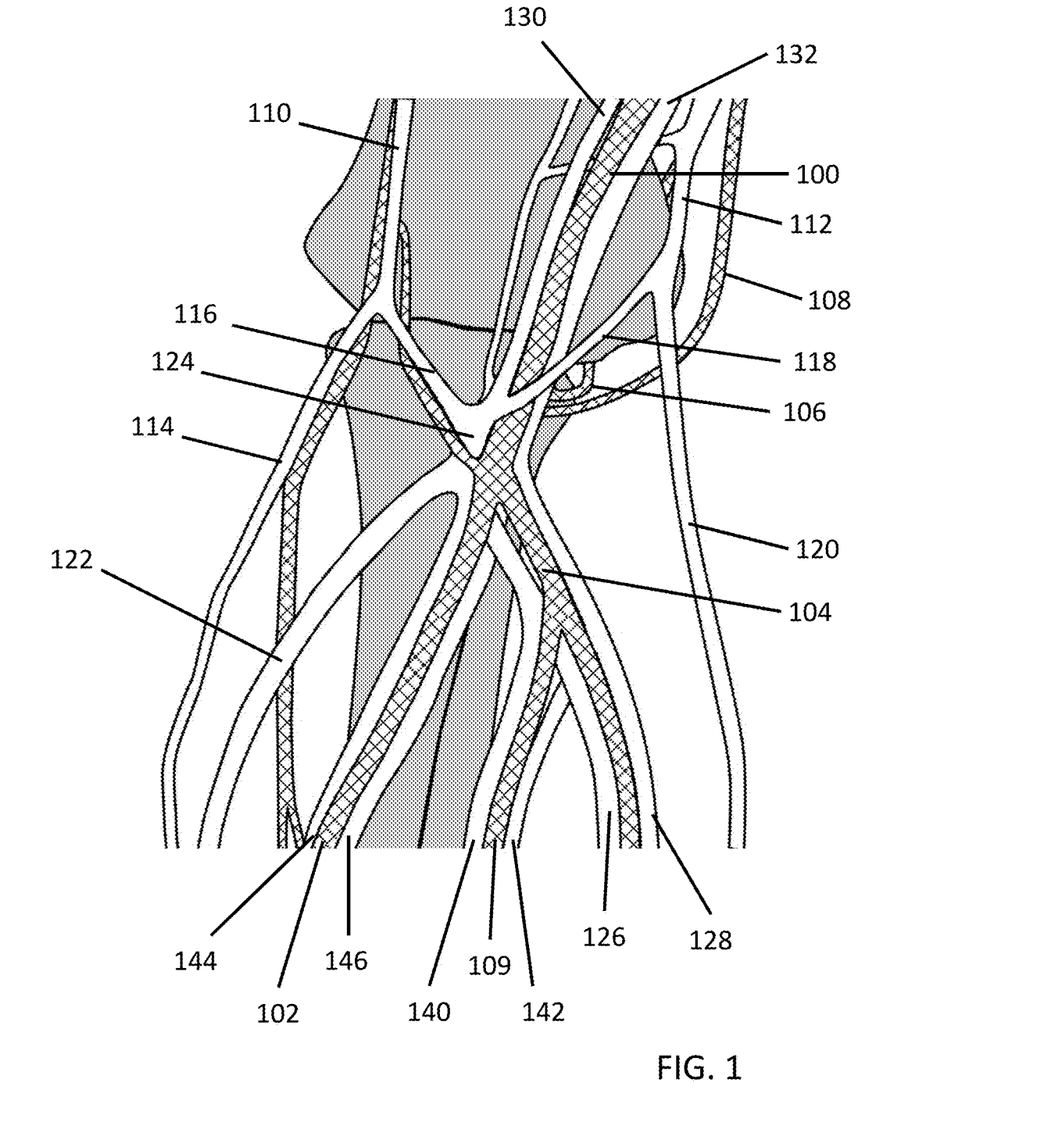
FIG. 1 is an illustrative depiction of the vascular anatomy of the arm.

FIG. 1 shows a simplified depiction of the typical vascular anatomy of the arm around the elbow. Specifically, FIG. 1 shows an anterior view of the right arm as would be seen with the palm facing upward. As shown there, the brachial artery (100) extends superficially and distally from the upper arm and sinks deeply into the arm near the elbow joint, where the brachial artery (100) branches into the radial artery (102) and the ulnar artery (104). The upper portion of the ulnar artery (104) is deeply seated within the arm beneath the superficial flexor muscles (not shown), and leads down the ulnar side of the forearm to the wrist. The anterior ulnar recurrent artery (106) and the posterior ulnar recurrent artery (108) branch off of the ulnar artery (104) just below the elbow joint, and these arteries supply blood to the joint and surrounding muscles. Further down the arm (typically just below the radial tuberosity of the radius bone (not shown)), the interosseous artery (109) branches off from the ulnar artery (104) and eventually feeds into the posterior and anterior interosseous arteries.

Also shown in FIG. 1 are the cephalic vein and the basilic vein. The cephalic vein runs along the outer border of the bicep muscle (not shown) continues down into the forearm (the cephalic vein of the upper arm is labeled in FIG. 1 as cephalic vein (110), while the cephalic vein of the lower arm is labeled as cephalic vein (114)). The median cephalic vein (116) joins the cephalic vein (110)/(114) near the elbow joint. The basilic vein runs along the inner side of the bicep muscle and continues into the forearm (the basilic vein of the upper arm is labeled as basilic vein (112), while the basilic vein of the lower arm is labeled as common ulnar vein (120)). The median cubital vein (118) (in some instances referred to as the median basilic vein) joins the basilic vein (112) and the common ulnar vein (120) (in some instances, this vein segment is also referred to as the basilic vein of the forearm or forearm basilica vein). The median cubital vein (118) and the median cephalic vein (116) are formed at the branching of the median antebrachial vein (122) (also known as the median vein). Near the branching of the median vein (122) into the median cubital vein (118) and the medial cephalic vein (116), a perforating branch (124) connects these vessels with the deep veins of the arm through the antebrachial fascia (not shown). As shown in FIG. 1, perforating branch (124) communicates with a first deep ulnar vein (126) and a second deep ulnar vein (128). These deep ulnar veins may run substantially parallel on either side of the ulnar artery (104) between the brachial artery (100) and the interosseous artery (109), and may branch away from ulnar artery (104) distal to the interosseous artery (109). Between the brachial artery (100) and the interosseous artery (109), the deep ulnar veins are typically located in close proximity to the ulnar artery, and usually less than 2 mm separate the ulnar artery from the deep ulnar veins. Along the length of the deep ulnar veins, transverse branches (not shown) may occasionally connect the deep ulnar veins. Also shown in FIG. 1 are first (130) and second (132) brachial veins. The brachial veins generally run along the brachial artery (100), and the deep ulnar veins feed into the brachial veins near the elbow joint. Additionally, a pair of radial veins ((144) and (146)) may run along the radial artery, and may feed into one or both of the brachial veins. Also shown in FIG. 1 are first (140) and second (142) interosseous veins, which may branch off from the first (126) and second (128) deep ulnar veins respectively, and which may run substantially parallel to the interosseous artery (109).

As mentioned above, the methods described here comprise forming a fistula between an ulnar artery and a deep ulnar vein. Preferably, the fistula is formed at a site in the proximal ulnar artery. As used herein, the term "proximal ulnar artery" means the ulnar artery between the brachial artery and branch of the interosseous artery. In some variations, the fistula may be formed between an ulnar artery and a deep ulnar vein at a location within about 6 cm from the branch between the brachial artery and the ulnar artery. In some of these variations, the fistula may be formed at a location less than about 4 cm from the branch between the brachial artery and the ulnar artery. Due to their deep anatomic location, the deep ulnar veins are difficult to access surgically, and thus are not desirable target sites for conventional surgical fistula-forming techniques. The deep anatomic location of the deep ulnar veins, however, means that these veins are usually undamaged (e.g., by needle sticks or other trauma), which may optimize fistula longevity. Additionally, because the deep ulnar veins feed into both the cephalic and basilic venous systems, forming a fistula between the ulnar artery and a deep ulnar vein may provide multiple upper-arm cannulation options for dialysis patients. As both of the deep ulnar veins feed into the cephalic and basilic venous systems, either deep ulnar veins may be selected, and in some instances each of the deep ulnar veins may be utilized to form different fistulas.

Generally, the methods described here comprise endovascularly advancing a distal portion of a first catheter into an ulnar artery, endovascularly advancing a distal portion of a second catheter into a first deep ulnar vein, and forming a fistula between the ulnar artery and the first deep ulnar vein. As mentioned above, the fistula is preferably formed between a proximal ulnar artery and a first deep ulnar vein, and thus the methods may comprise endovascularly advancing a distal portion of a first catheter into a proximal ulnar artery, endovascularly advancing a distal portion of a second catheter into a first deep ulnar vein, and forming a fistula between the proximal ulnar artery and the first deep ulnar vein. When catheters are endovascularly advanced into an ulnar artery and/or a deep ulnar vein, access to these vessels may be achieved in any suitable manner, as will be described in more detail below. The first and second catheters may be aligned to position one or more fistula-forming elements (e.g., one or more electrodes, mechanical cutting elements, chemical mechanisms, cryogenic-cautery devices, laser ablation devices, combinations thereof, and the like, as will be described descried in more detail below) relative to the desired fistula site. One or both of the first and second catheters may be advanced or retracted within their respective blood vessels to axially position the one or more fistula-forming elements relative to the fistula-formation site. One or both of the first and second catheters may be rotated to rotationally position the one or more fistula-forming elements relative to the fistula-formation site (e.g., to direct a fistula-forming element in the ulnar artery toward a deep ulnar vein, to direct a fistula-forming element in a deep ulnar vein toward the ulnar artery, to direct a fistula-forming element in the ulnar artery toward a fistula-forming element in a deep ulnar vein, etc.). The methods described here may comprise using one or more magnets, markers, and/or other alignment elements to assist in positioning the first and/or second catheters, as will be described in more detail below. Once the one or more fistula-forming elements are positioned relative to the fistula-formation site, the fistula-forming elements may be actuated to cut, ablate, or otherwise remove tissue between the ulnar artery and the deep ulnar vein to form a fistula therebetween.

Following activation of the fistula-forming element, one or more steps may be conducted to assess the condition of the fistula. For example, in some variations a radiopaque dye (or other suitable contrast media) may be introduced into the ulnar artery to confirm blood flow into the deep ulnar vein from the ulnar artery following activation of the fistula-forming element. In some of these variations, the first and/or second catheters may be removed from their respective vessels prior to introduction of the radiopaque dye into the ulnar artery. In other variations, the radiopaque dye may be introduced into the ulnar artery through the first catheter. In some variations, formation of the fistula may act to release one or more radiopaque agents from the first and/or second catheters. For example, in some variations, a first catheter advanced into an ulnar artery may comprise a fistula-forming element, and a second catheter advanced into a deep ulnar vein may comprise a balloon housing a radiopaque agent therein. The first and second catheters may be aligned such that activation may form a fistula between the ulnar artery and deep ulnar vein and also punctures the balloon to release the radiopaque agent.

The methods described here may further comprise forming a second fistula between the ulnar artery and a second deep ulnar vein. For example, if a user or physician determines that there is insufficient flow between the ulnar artery and a first deep ulnar vein, a second fistula may be formed between the ulnar artery and a second deep ulnar vein. The second fistula may be formed during the same procedure, or may be formed during a subsequent procedure. The second fistula may be formed using any of the methods described hereinthroughout.

Because the deep ulnar veins feed into both the cephalic and basilic systems, a patient having a fistula between an ulnar artery and a deep ulnar vein may be cannulated using a blood vessel from either system to provide dialysis access. In some variations, the methods described here may comprise allowing a fistula formed between an ulnar artery and a deep ulnar vein to mature (this may take as long as six or more months), and cannulating either the cephalic and basilic systems to provide vascular access. The methods may further comprise assessing the flow through a vein of the cephalic or basilic system, selecting a vein having a flow rate suitable for dialysis access (which is some instances may be approximately 600 ml/min), and cannulating that vein to provide vascular access. In some variations, this may comprise cannulating a portion of the median cubital vein. In some variations, this may comprise cannulating a portion of the cephalic vein. In other variations, this may comprise cannulating a portion of the basilic vein. In some variations, both the cephalic and basilic veins may be cannulated, as will be described in more detail below. In variations where the cephalic vein is cannulated, the methods may further comprise ligating or coil embolizing the median cubital vein to prevent or reduce flow from the fistula into the basilic vein. Conversely, in variations where the basilic vein is cannulated, the methods may comprise ligating or coil embolizing the median cephalic vein to reduce flow from the fistula into the cephalic vein.

In some variations, the methods may further comprise ligating or coil embolizing at least one brachial vein. In these variations, one or both of the brachial veins may be ligated or coil embolized. Restricting flow through the brachial veins may divert flow to cephalic and/or basilic systems, which may improve flow therethrough. In these variations, the brachial vein or veins may be closed off during the same procedure in which the fistula is formed, or may be closed off during a later procedure (e.g., between about four weeks and about eight weeks following formation of the fistula). In some variations, a first brachial vein may be closed off during the fistula-forming procedure, while a second brachial vein may be closed during a subsequent procedure.

It should be appreciated that the methods described here may be used to form a fistula between the ulnar artery and deep ulnar vein that may not require a stent or other connecting structure to maintain patency of the fistula. In some variations, however, the methods described here may further comprise placing a stent, tube, or other structure between the ulnar artery and deep ulnar vein. Additionally, while the methods described immediately above may comprise advancing catheters into both the ulnar artery and a deep ulnar vein, respectively, it should be appreciated that in some variations a fistula may be formed using only a first catheter placed in a deep ulnar vein, or may be formed using only a first catheter placed in the ulnar artery. When a first catheter is placed in the ulnar artery and a second catheter is placed in a deep ulnar vein, either catheter or both catheters may comprise one or more fistula-forming elements. When a first catheter placed in the ulnar artery comprises a fistula-forming element, that fistula-forming element may form the fistula directionally from the ulnar artery into the deep ulnar vein. When a second catheter placed in the ulnar artery comprises a fistula-forming element, that fistula-forming element may form the fistula directionally from the deep ulnar vein into the ulnar artery. When both first and second catheters comprise fistula-forming elements, the fistula may be formed directionally from the deep ulnar vein into the ulnar artery, directionally from the ulnar artery into a deep ulnar vein, or may be formed simultaneously from both the ulnar artery and a deep ulnar vein.

Figure 2:
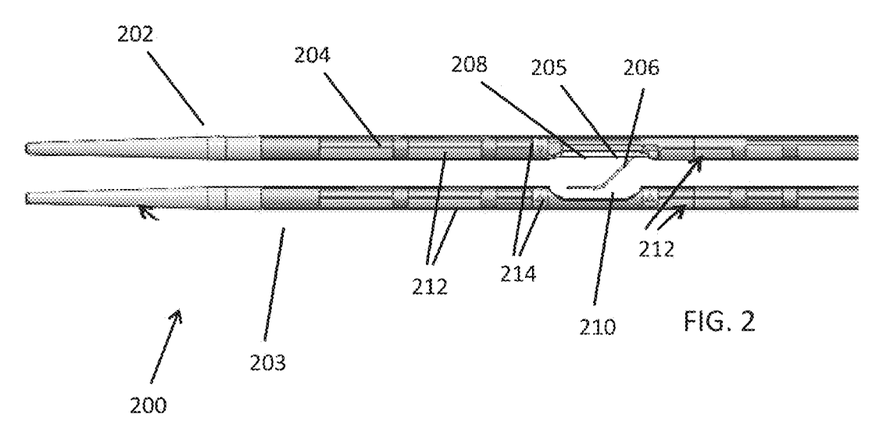
FIG. 2 depicts a variation of a catheter system suitable for use with the methods described here.

Any suitable catheter or catheters may be used to form the fistulas using the methods described here. The methods described here may use one or more of the devices as described in U.S. patent application Ser. No. 13/298,169, filed on Nov. 16, 2011 and titled "DEVICES AND METHODS FOR FORMING A FISTULA," which is hereby incorporated by reference in its entirety. In some variations, a fistula may be formed using a first catheter placed in the ulnar artery and a second catheter placed in the deep ulnar vein. FIG. 2 show one variation of a catheter system (200) that may be used to form a fistula between the ulnar artery and a deep ulnar vein. As shown there, system (200) may comprise a first catheter (202) and a second catheter (203). The first catheter (202) may comprise a catheter body (204) and an electrode (206) which may be advanced out of an opening (205) in the catheter body (204). Current may be passed through the electrode (206) to ablate or otherwise remove tissue contacted by the electrode (206). In some variations, the first catheter (202) may comprise an insulating housing (208) (e.g., a ceramic housing or the like) within the catheter body, which may help protect other components of the first catheter (202) from heat that may be generated by the electrode (206) during tissue removal. The electrode (206) may be selectively moved from a position in which the electrode (206) is retained or otherwise held in the catheter body (204) to a position in which the electrode (206) extends away from the catheter body (204) (such as shown in FIG. 2), and electrode (206) may also be selectively moved back to a retracted/low-profile position (either the same or a different position as the previous retracted position) following ablation of tissue. In some variations, the electrode (206) may be biased toward an extended position when not otherwise restrained by the catheter body (204). While a fistula-forming element comprising an electrode (206) is shown in FIG. 2, it should be appreciated that the methods described here may utilize a catheter comprising any suitable fistula-forming element (e.g., one or more electrodes/electrocautery mechanisms, cone or more mechanical cutting mechanisms such as blades, lances, needles, or the like, one or more chemical devices, cryogenic-cautery devices, laser ablation devices, combinations thereof and the like), such as those described in more detail in U.S. patent application Ser. No. 13/298,169, which was previously incorporated by reference in its entirety, and may be operated in any manner as described therein.

While shown in FIG. 2 as having both first (202) and second (203) catheters, system (200) need not comprise two catheters. For example, in variations of the methods described here in which a fistula is formed using a catheter placed only in the ulnar artery or only in a deep ulnar vein, the system (200) may comprise only a first catheter (202). In variations that do have a second catheter (203), the catheter (203) may have any suitable elements or combination of elements. For example, the second catheter (203) may comprise a catheter body (208) having a recess (210) extending therein. The recess (210) may be coated by an insulating material (not shown), which may act as a backstop to receive and contact the electrode (206) of the first catheter without damaging one or more components of the first catheter (202). Additionally or alternatively, the second catheter (203) may comprise one or more fistula-forming elements, which may be the same as or different from the fistula forming element or elements of the first catheter (202).

The methods described here may utilize one or more catheters comprising one or more alignment elements, which may help to position catheters within the vasculature. For example, in some variations a method may comprise using one or more alignment elements to help bring two or more catheters (and with them, associated blood vessels) in closer approximation. Additionally or alternatively, a method may comprise using one or more alignment elements to position one or more catheters in a specific rotational configuration relative to the blood vessels and/or the other catheters. Additionally or alternatively, a method may comprise using one or more alignment elements to position one or more catheters axially within a blood vessel or blood vessels. For example, one or more alignment elements may be configured to position a fistula-forming element of a catheter relative to the ulnar artery and a deep ulnar vein such that activation of the fistula-forming element directs fistula formation between the two vessels.

In some variations, a catheter may comprise one or more magnetic alignment components. Examples of magnet arrangements for use with the catheters described here may be found in U.S. patent application Ser. No. 13/298,169, which was previously incorporated by reference in its entirety. These magnetic alignment components may be attracted to one or more additional elements (e.g., one or more portions of a second catheter, one or more magnets or other components placed externally from the body) to help position or align the catheter within a vessel. For example, one or more magnets placed outside of the body may interact with the magnetic alignment components of a catheter to help facilitate advancement of the catheter through the vasculature. Additionally or alternatively, one or more magnetic alignment elements of a first catheter may interact with one or more magnetic alignment elements of a second catheter to attract the first and second catheters toward each other, and/or to bias the first and second catheters toward a specific rotational and/or axial alignment.

For example, in the variation of system (200) shown in FIG. 2, each of first (202) and second (203) catheters may comprise a plurality of magnetic alignment elements (212). These magnetic alignment elements (212) may be configured to bias the axial positioning of the first (202) and second (203) catheters such that the opening (205) of the first catheter (202) axially aligns with the recess (210) of the second catheter (203). The magnetic alignment elements (212) may also be configured to bias the rotational positioning of the first (202) and second (203) catheters such that the opening (205) of the first catheter (202) faces toward the recess (210) of the second catheter (203). Accordingly, the magnetic alignment elements (212) may be used to help position the first (202) and second (203) catheters within respective blood vessels such that the electrode (206) may be extended from opening (205) toward recess (210) of the second catheter (203) during fistula formation.

Additionally or alternatively, in some variations, the catheter may comprise one or more shape-changing elements for approximating two or more blood vessels. In these variations, the shape-changing element may have a first configuration during advancement of the catheter through the vasculature. Once the catheter reaches a target location, the shape-changing element may be altered to a second configuration, which may alter the overall shape of the catheter. As the catheter changes shape, the catheter may move or reconfigure one or more portions of the blood vessel, which may help bring that portion or portions of the blood vessel in closer approximation to one or more portions of a second blood vessel. Examples of shape-changing elements for use with the catheters described here may be found in U.S. patent application Ser. No. 13/298,169, which was previously incorporated by reference in its entirety.

Additionally or alternatively, the methods may comprise visualizing one or more markers from one or more catheters during advancement and positioning thereof. In some variations, the marker may be directly visualized. In other variations, the marker may be indirectly visualized (e.g., via ultrasound, fluoroscopy and/or X-ray visualization). Markers may be located anywhere relative to the catheter, e.g., one or more surfaces of the catheter, inside of the catheter. In some variations, one or more portions of the catheter may be made from an echogenic or radiographic material. A marker may be attached to the catheter by any suitable method, for example, by mechanical attachment (e.g., embedded in a portion of the catheter, circumferential circumscription, or the like), adhesive bonding, welding, soldering, combinations thereof or the like. For example, in the variation of system (200) shown above in FIG. 2, each of the first (202) and second (203) catheters may comprise one or more markers (214). These markers (214) may be visualized during advancement and/or position of the first (202) and second (203) catheters to confirm that the catheters are properly positioned within the blood vessels. For example, in variations where a method comprises axially aligning the opening (205) of the first catheter (202) relative to the recess (210) of the second catheter (203) and/or rotationally aligning the opening (205) of the first catheter (202) relative to the recess (210) of the second catheter (203), the method may further comprise visualizing one or more markers (214) of the first (202) and/or second (203) catheters to confirm this positioning.

In some variations, one or more of the catheters may comprise one or more balloons or other expandable structures. These expandable structures may serve one or more functions. In some instances, an expandable structure may help appose an electrode surface (or other fistula-forming element) against one or more vessel walls. This apposition may help temporarily flatten or otherwise relocate tissue, and may act to displace blood from the area. Additionally, during fistula formation, the expandable member may continue to urge the fistula forming element against tissue as it is removed from the vessel wall. In some variations, the expandable structure may be configured to help provide apposition between the catheter and a vessel wall, while still allowing for blood flow through the blood vessel. In some instances, one or more expandable structures may help modify or otherwise alter the size or shape of a fistula. In still other instances, the expandable structures may be used to dilate, contract, or otherwise displace a portion of one or more blood vessels. In some of these variations, this displacement may help bring a portion of the blood vessel closer to a skin surface.

Figure 3A:
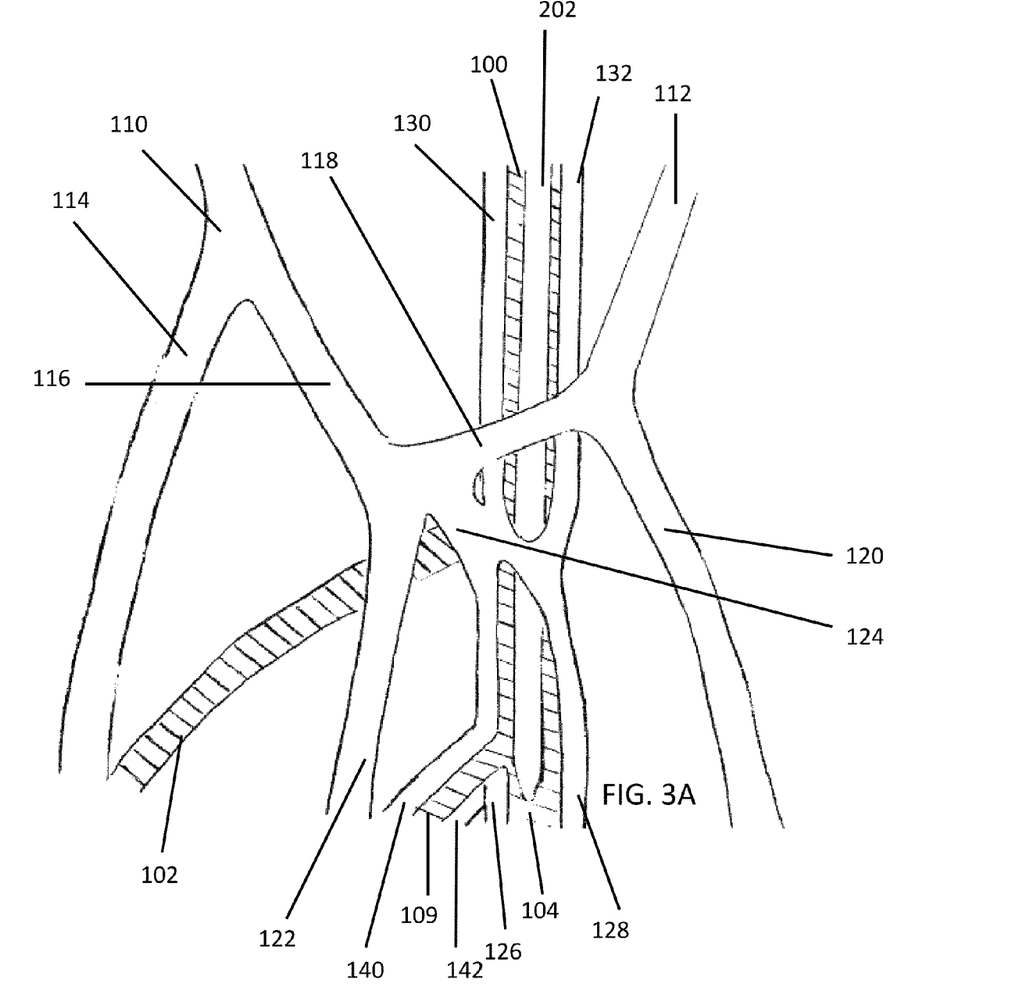
FIGS. 3A-3C depict an illustrative method as described here.
Figure 3B:
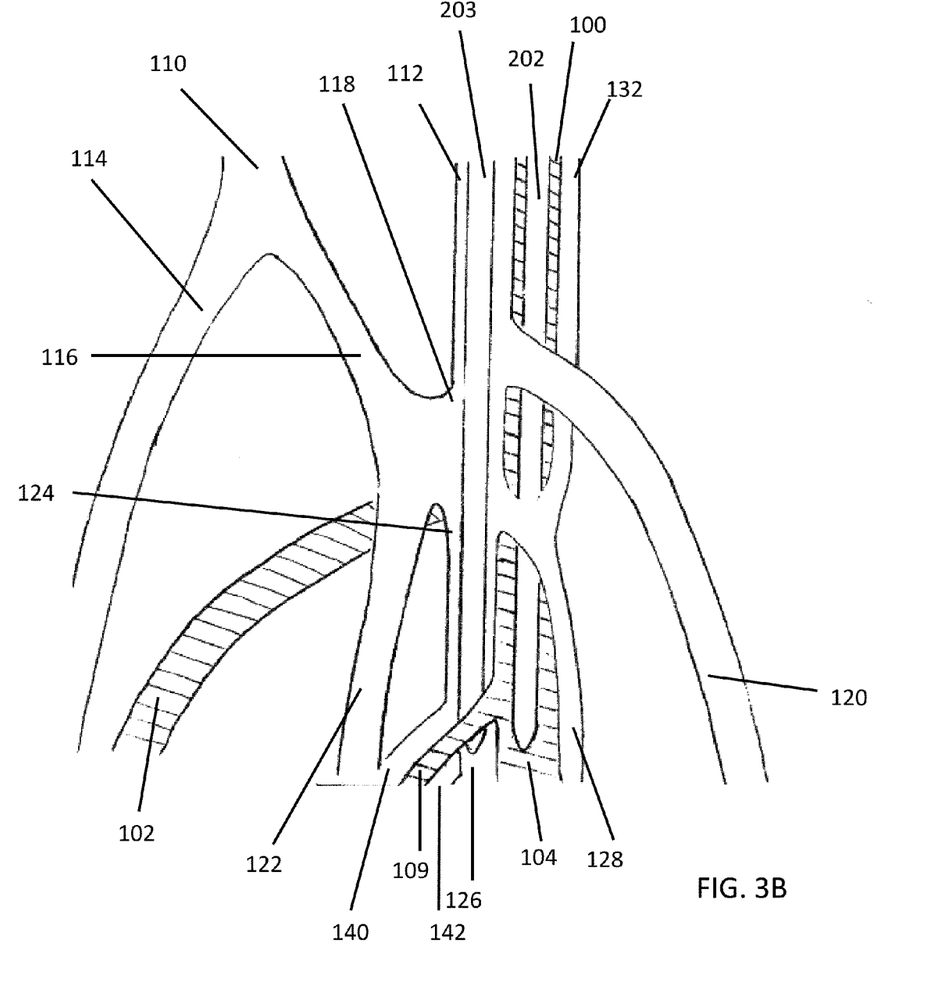
Figure 3C:
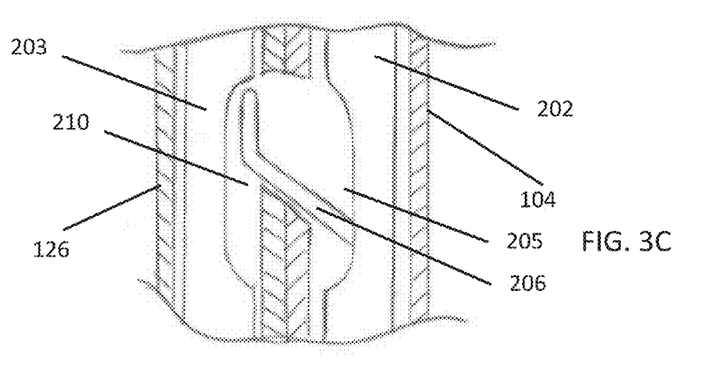

FIGS. 3A-3C depict an illustrative method by which the catheter system (200) of FIG. 2 may be used to form a fistula between a first deep ulnar vein and an ulnar artery. The labeling of FIGS. 1 and 2 will be used for common elements and anatomical locations. As shown in FIG. 3A, the method may comprise endovascularly advancing a distal portion of a first catheter (202) into an ulnar artery (104). In the method shown in FIG. 3A, the first catheter (202) may be advanced into the ulnar artery (104) from the brachial artery (100). In some variations, the method may comprise creating an access site (not shown) in the brachial artery (100), and advancing the first catheter (202) into the brachial artery (100) through the access site. It should be appreciated, however, that the first catheter (202) may be advanced into the ulnar artery in any suitable manner, as described in more detail below.

As shown in FIG. 3B, the method may further comprise endovascularly advancing a second catheter (203) into a first deep ulnar vein (126) (it should be appreciated that the second catheter (203) may be advanced into either of the deep ulnar veins (126) or (128)). In the method shown in FIG. 3B, the second catheter (203) may be advanced into the first deep ulnar vein (126) from the perforating branch (124), which may be accessed by advancing the second catheter (203) through the basilic vein (112) and the median cubital vein (118). In some variations, the method may comprise creating an access site (not shown) in the basilic vein (112), and advancing the second catheter (203) into the basilic vein (112) through the access site. It should be appreciated, however, that the second catheter (203) may be advanced into the deep ulnar vein (126) in any suitable manner, as described in more detail below. While the first catheter (202) is shown in FIG. 3A as being advanced into ulnar artery (104) prior to advancement of the second catheter (203) into the deep ulnar vein (126), it should be appreciated that the first (202) and second (203) catheters may be advanced in any order.

Once the distal ends of the first (202) and second (203) catheters have been advanced into the ulnar artery (104) and deep ulnar vein (126), the first (202) and second (203) catheters may be axially positioned relative to one another to align the opening (205) of the first (202) catheter with the recess (210) of the second catheter (203), as shown in FIG. 3C. Additionally, the first (202) and second (203) catheters may be axially positioned relative to the ulnar artery (104) and deep ulnar vein (126) respectively such that the opening (205) of the first catheter (202) and recess (210) of the second catheter (203) are axially aligned with the desired fistula formation site. In some instances, when the opening (205) of the first catheter (202) and recess (210) of the second catheter (203) are axially aligned with the desired fistula formation site (e.g., in a ulnar artery and a deep ulnar vein), the distal tips of the first and second catheters may extend into the ulnar artery (104) and deep ulnar vein (126) distally of the branching of the interosseous artery (109) and the interosseous veins (e.g. the first interosseous vein (140)), such as shown in FIG. 3B. Alternatively, when the opening (205) of the first catheter (202) and recess (210) of the second catheter (203) are axially aligned as discussed above, a distal tip of the first catheter (202) may extend into the interosseous artery (109) and/or the distal tip of the second catheter (203) may extend into an interosseous vein (e.g., first interosseous vein (140)).

Additionally, the first (202) and second (203) catheters may be rotationally aligned such that opening (205) may face the recess (210) of the second catheter (203). As mentioned above, in some variations, the methods may comprise using one or more magnetic alignment elements (212) help achieve the axial or rotational positioning of the first (202) and second (203) catheters. Additionally or alternatively, the positioning of the first (202) and second (203) catheters may be confirmed by visualizing markers (214) of the first and/or second catheters.

Once the first (202) and second (203) catheters are positioned relative to each other and their respective vessels, the electrode (206) may be advanced out of the opening (205) of the first catheter (202) to press the electrode (206) against a vessel wall of the ulnar artery (104). Energy may be delivered to the electrode (206) to cut tissue, which may advance the electrode (206) from the ulnar artery (104), through the wall of the deep ulnar vein (126), and into the deep ulnar vein (126). In some variations, the first catheter (202) comprising the electrode (206) may be placed in the deep ulnar vein (126) and the second catheter (203) may be placed in the ulnar artery (104), such that the electrode (206) may be advanced from the deep ulnar vein (126) into the ulnar artery (104). Once the fistula has been has been formed between the ulnar artery (104) and the deep ulnar vein (126), one or more contrast agents may be passed through the fistula and/or a second fistula may be formed, such as described in more detail above.

It should be appreciated that in some or all of the methods described here, one or more portions of the patient may be immobilized during some all of the steps of the method. For example, when a fistula is formed between two vessels in an arm, one or more portions of the arm (e.g., a wrist, an elbow, or the like) may be immobilized. In some of these variations, a wrist of the patient may be immobilized. When a wrist is immobilized, the wrist may be immobilized prior to creating access to one or more blood vessels. In some of these variations, the wrist may remain immobilized until after formation of the fistula. It should be appreciated that when a portion of the arm is immobilized, the arm may be temporarily released to reposition the arm, if needed.

Figure 4A:
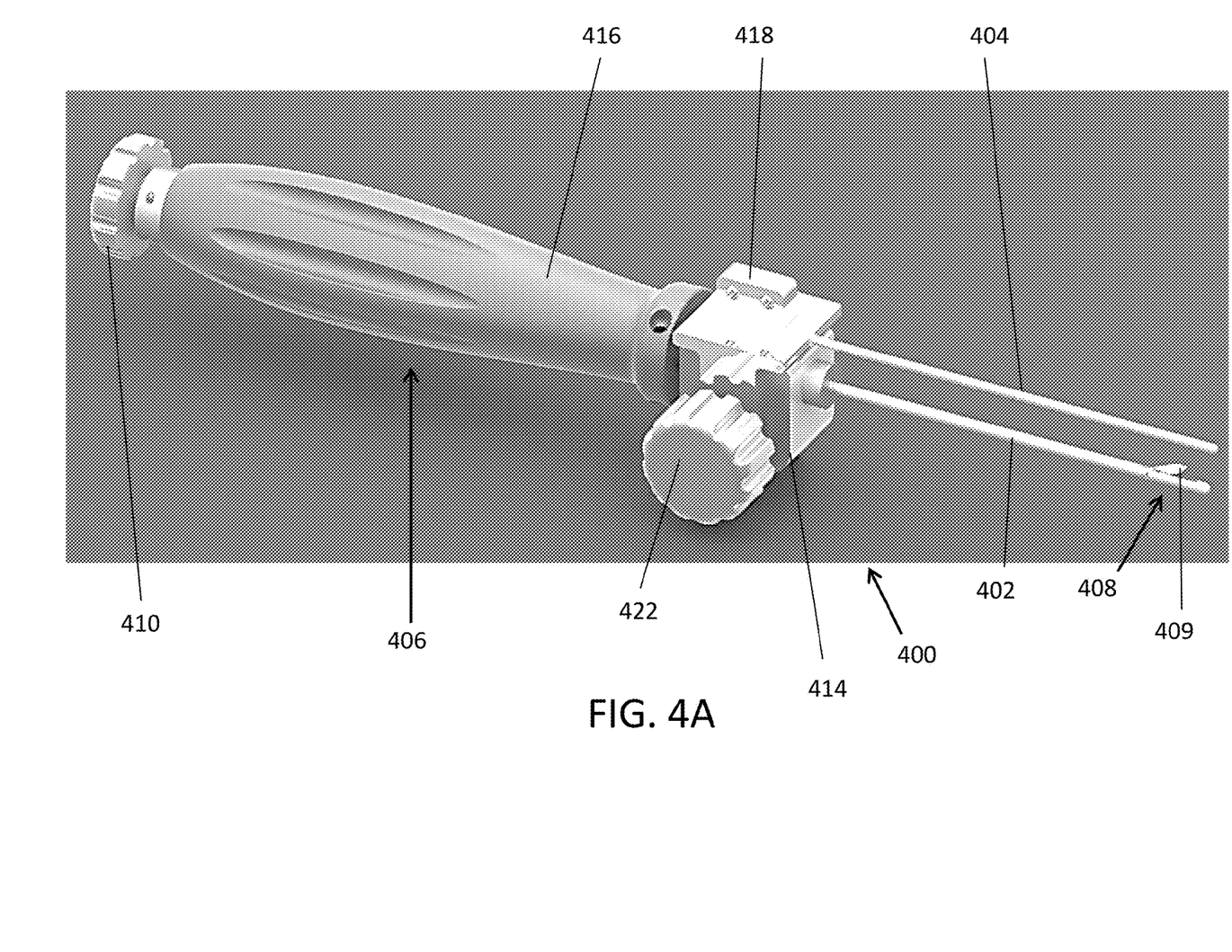
FIGS. 4A-4C depict a variation of a device described here for forming a fistula.
Figure 4B:
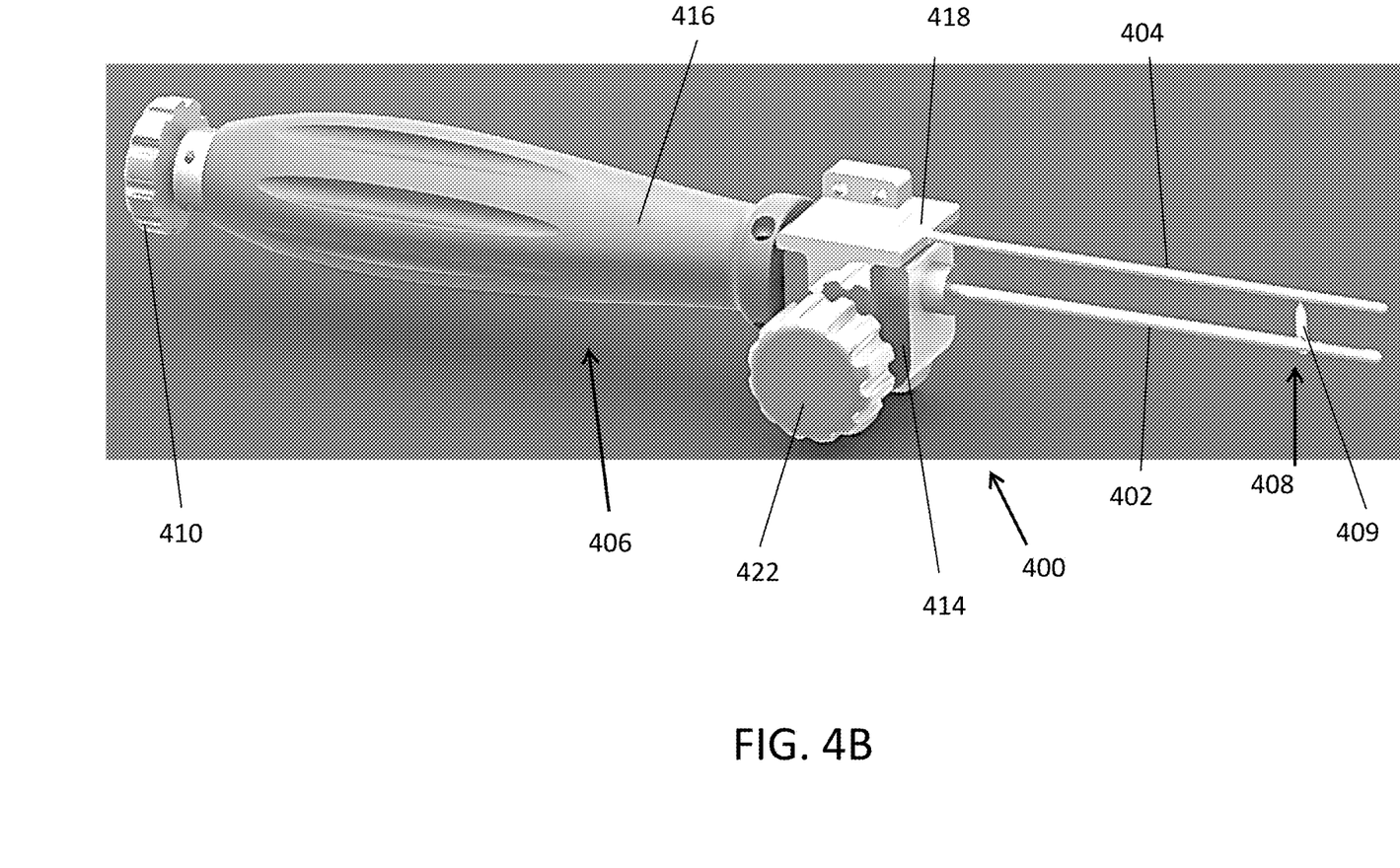
Figure 4C:
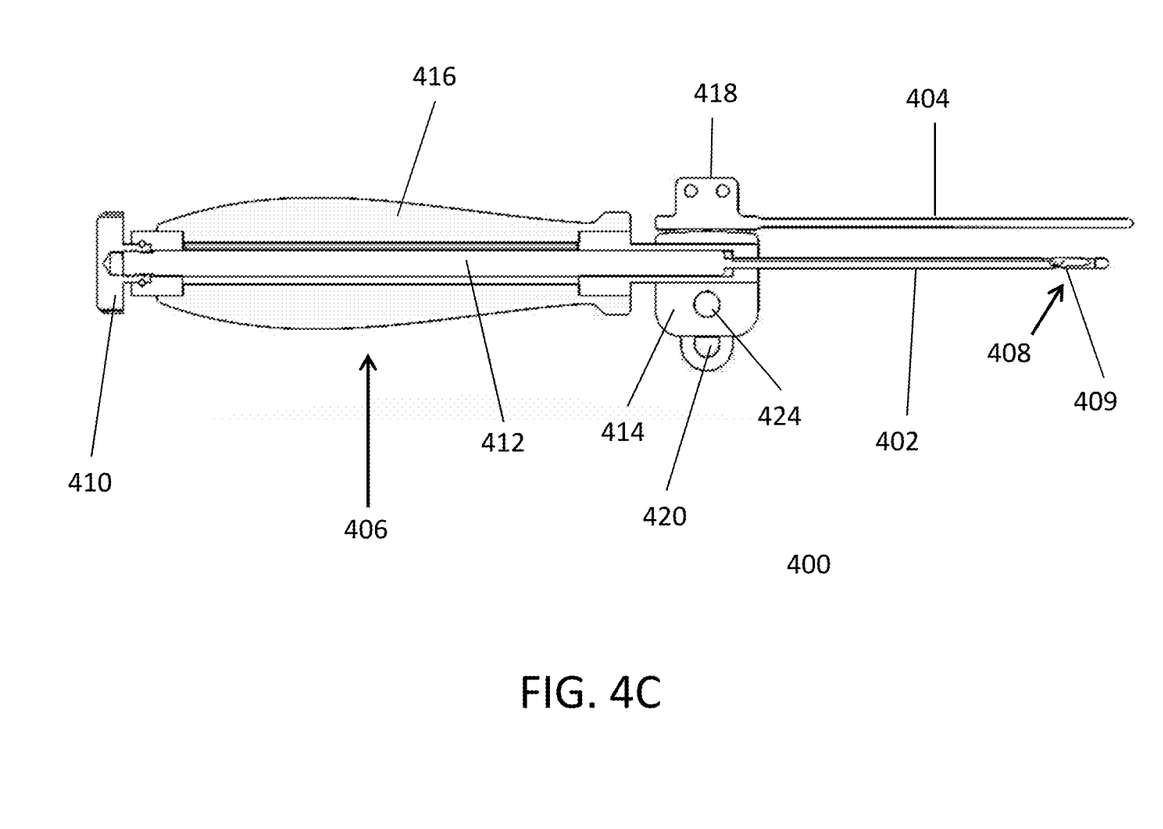

FIGS. 4A and 4B depict perspective views and 4C depicts a cross-sectional side view of a device (400) which may be used to form a fistula. While the device (400) may be used to form a fistula between two or more vessels as described above, the device (400) may be used to form a fistula between any two vessels, such as described here and in U.S. patent application Ser. No. 13/298,169, which was previously incorporated by reference in its entirety. As shown in FIG. 4A, the device (400) may comprise a first arm (402), a second arm (404), a handle (406), and a fistula-forming element (408). Generally, the first arm (402) and the second arm (404) may be formed from one or more rigid materials (e.g., one or more metals such as stainless steel, one or more plastics, combinations thereof and the like), such that when each arm is positioned in a respective blood vessel, the vessel may substantially conform to the shape of the arm.

In the variation shown in FIGS. 4A-4C, the handle (406) may comprise a connection portion (414) and a grip portion (416). The grip portion (416) may be sized and configured such that it may be held by a user, and may have any suitable dimensions. For example, in some variations the grip portion (416) may have any suitable length (e.g., between about 8 cm and about 25 cm, between about 12 cm and about 20 cm, or the like) and any suitable diameter (e.g., between about 3 cm and about 12 cm, between about 5 cm and about 8 cm, and the like). The connection portion (414) (which may be connected to a distal end of the grip portion (416)) is generally configured to position the first (402) and second (404) arms relative to each other. As shown there, the first arm (402) may be fixedly connected to the connection portion (414) and the second arm (404) may be adjustably connected to the connection portion (414). Specifically, a proximal end of the second arm (414) may comprise a connector (418) having a track (420) (as illustrated in a cross-sectional side view in FIG. 4C), and a knob (422) may connect the connector (418) to the connection portion (414). Specifically, the knob (422) may comprise a pin (424) which may extend through the track (420) and into the connection portion (414). The knob (422) may be rotated in a first direction to lock the connector (418) relative to the connection portion (414), and may be rotated in a second direction to allow the connector (418) to be adjusted relative to the connection portion (414).

When the connector (418) is adjustable relative to the connection portion (414), the track (420) may be rotated and/or slid relative to the pin (424). Rotation of the connector (418) may rotate the second arm (404) relative to the first arm (402), while sliding of the connector (418) may adjust the distance between the second arm (404) and the first arm (402). Accordingly, the position of the second arm (404) may be adjusted to set a specific relation between the first arm (402) and the second arm (404), and the knob (422) may be adjusted to temporarily lock the position of the second arm (404) relative to the first arm (402). When the first arm (402) and the second arm (404) are placed in first and second vessels, respectively, the relative positioning between the first and second arms may also dictate the relative positioning between the first and second vessels.

The fistula-forming element (408) may be any suitable fistula-forming element (e.g., a cutting mechanism, an electrode) as described in more detail above. In the variation shown in FIGS. 4A-4C, the fistula-forming element may comprise a blade (409) connected to the first arm (402). The blade (409) may be rotatable between a low-profile configuration in which the blade (409) is housed within the first arm (402) (as shown in FIG. 4C) and a cutting configuration in which the blade (409) extends from the first arm (402) (as shown in FIG. 4B). As the blade (409) rotates out of the first arm (402), a cutting edge of the blade (409) may cut tissue. In some variations, the blade (409) may also act as an electrode to deliver current to tissue. The blade (409) may be rotated in any suitable manner. In the variation of the device (400) shown in FIGS. 4A-4C, the device (400) may comprise a blade control knob (410). The blade control knob (410) may be connected to a linkage (412), which in turn may be connected to the blade (409). The linkage (412) may be configured such that rotation of the control knob (410) in a first direction advances the linkage (412), which in turn rotates the blade (409) from the low-profile configuration to the cutting configuration. Conversely, rotation of the control knob (410) in a second direction may retract the linkage (412), which in turn may rotate the blade (409) from the cutting configuration to the low-profile configuration. While the fistula-forming element (408) is shown in FIG. 4A as being connected to the first arm (402), it should be appreciated that in some instances the fistula-forming element (408) may be connected to the second arm (404), and in other instances both the first arm (402) and the second arm (404) may comprise a fistula-forming element.

As mentioned above, the device (400) may be used to form a fistula. In these variations, the first arm (402) may be introduced into a first blood vessel and the second arm (404) may be introduced into a second blood vessel. The position of the second arm (404) relative to the second arm (402) may be adjusted to reposition the second blood vessel relative to the first blood vessel. When the blood vessels are positioned as desired, the second arm (404) may be fixed relative to the first arm (402) (e.g., by rotating the knob (422)). With the arms set in a fixed relation, the fistula-forming element (408) may be activated to form a fistula. For example, this may comprise rotating the blade (409) relative to the first arm (402) to cut tissue of the first and second blood vessels positioned between the first arm (402) and the second arm (404).

Ulnar Artery Access

In variations where a catheter or other tool is advanced endovascularly into the ulnar artery, access to the ulnar artery may be achieved in any suitable manner. In some variations, the catheter may be advanced along the brachial artery and into the ulnar artery. In some of these methods, the catheter may be introduced into the vasculature via a brachial access site. In some of these methods, the brachial artery may be cannulated with a cannula directed distally in the brachial artery. The cannula may be any suitable size (e.g., about 5 Fr, about 7 Fr, between about 5 Fr and about 7 Fr), and may be introduced into the brachial access site in any suitable manner, for example, using Seldinger technique, a micropuncture set, and/or a cutdown procedure. In other variations, the catheter may be advanced along the brachial artery from an access site upstream of the brachial artery. For example, the catheter may introduced into the vasculature via a femoral artery access site, and may be advanced to the brachial artery therefrom. In some variations, the ulnar artery may be accessed directly. In some of these variations, an ulnar access site may be formed in the ulnar artery (e.g., at a distal location in the wrist or forearm where the ulnar artery is superficially positioned), and a catheter may be advanced in a retrograde fashion through the ulnar access site. In these variations, the ulnar artery may be cannulated as described above. In still other variations, a catheter or other tool may be advanced endovascularly into the ulnar artery through an access site in the radial artery.

The catheter may be advanced into the ulnar artery using one or more visualization techniques (e.g., via fluoroscopy, ultrasound, combinations thereof, or the like). In some variations, the catheter may be advanced over or along a guidewire which may be placed at the target fistula formation site via one or more of the vascular access sites described immediately above.

Deep Ulnar Vein Access

In variations where a catheter or other tool is advanced endovascularly into a deep ulnar vein, access to the deep ulnar vein may be achieved in any suitable manner. In some variations, the catheter is introduced into the vascular site via an access site. A vascular access site may be formed using a micropuncture set, an access needle (e.g., a 18 or 19 gauge access needle), and/or using a surgical cut-down procedure, such that a cannula may be placed in the blood vessel. The venous access site may be in any suitable blood vessel, such as the basilic vein, the cephalic vein, or a brachial vein.

In some variations, the catheter may be advanced to a deep ulnar vein endovascularly along the median cubital vein. For example in some variations, the catheter may be advanced along the basilic vein, into the median cubital vein, and into one of the deep ulnar veins via the perforating branch extending between the median cubital vein and the deep ulnar veins. In instances where the perforating branch extends between the deep ulnar veins and the median antebrachial vein, the catheter may be advanced from the median cubital vein into the median vein, then into one of the deep ulnar veins.

In other variations, the catheter may be advanced to a deep ulnar vein endovascularly along the median cephalic vein. For example, in some variations, the catheter may be advanced into the vasculature through an access site in the cephalic vein, and may be endovascularly advanced from the cephalic vein into the median cephalic vein, and into one of the deep ulnar veins via a perforating branch (to access the perforating branch, it may be necessary to advance the catheter into either the median cubital vein or the median antebrachial vein).

In still other variations, the catheter may be advanced to a deep ulnar vein endovascularly along a brachial vein. For example, in some variations, the catheter may be advanced into the vasculature through an access site in a brachial vein, and may be endovascularly advanced from the brachial vein into one of the deep ulnar veins in a retrograde fashion.

The catheter may be advanced into the deep ulnar vein using one or more visualization techniques (e.g., via fluoroscopy, ultrasound, combinations thereof, or the like). In some variations, the catheter may be advanced over or along a guidewire which may be placed at the target fistula formation site via one or more of the vascular access sites described immediately above.

Dialysis Access

As mentioned above, one or more veins may be cannulated following fistula formation to provide dialysis access. Generally, providing dialysis access comprises cannulating one or more blood vessels with a first needle and a second needle. Generally, one of the needles may be an arterial needle configured to supply blood to a dialysis machine, while the other needle may be a venous needle configured to return blood to the patient. In some variations, both the first and second needles may be placed in the cephalic vein. In other variations, both the first and second needles may be placed in the basilic vein. In still other variations, both the first and second needles may be placed in the median cubital vein. When both the first and second needles are placed in the same vein segment, it may be desirable to place the arterial and venous needles such that they are at least about 5 cm apart, which may reduce the likelihood that blood returned to the patient through the venous needle is taken up by the arterial needle.

In other variations, the first and second needles may be positioned in different blood vessels. In some variations, a first needle may be placed in a basilic vein and a second needle may be placed in a median cubital vein (e.g., an arterial needle may be placed in the median cubital vein and a venous needle may be placed in the basilica vein). In other variations, a first needle may be placed in a cephalic vein and a second needle may be placed in a median cubital vein (e.g., an arterial needle may be placed in the median cubital vein and a venous needle may be placed in the cephalic vein). In still other variations, a first needle may be placed in a cephalic vein and second needle may be placed in a basilic vein (e.g., an arterial needle may be placed in the basilic vein and a venous needle may be placed in the cephalic vein). In these variations, the needle placed in the cephalic vein may be either the arterial needle or the venous needle. When a first needle and second needle are positioned in different blood vessels (e.g., when a first needle is placed in the basilic vein and a second needle is placed in the antecubital vein or the cephalic vein), there may be a reduced likelihood that blood returned to the body via the venous needle (which may be either the first or second needle) may be taken up by the arterial needle.

Example 1

A total of nine patients received a percutaneously-formed fistula between a proximal ulnar artery and a deep ulnar vein of an arm of each patient. To form the fistula, a first catheter carrying an electrode was percutaneously positioned in the deep ulnar vein (via brachial vein access) and a second catheter was percutaneously positioned in the proximal ulnar artery (via brachial artery access), and the electrode ablated tissue between the deep ulnar vein and the proximal ulnar artery to remove tissue between the vessels. The arm was immobilized at the wrist during the formation of the fistula. Patient follow-ups occurred at one month, two months, and three months. At the first follow-up, one or more vessels were coil embolized in some patients at the discretion of the physician.

As shown in Table 1, a fistula was successfully formed in nine of nine patients. For the nine patients, the average time to dialysis readiness was 62 days. Dialysis readiness was determined based on successful initiation of dialysis or physical determination of a flow rate of at least 300 ml/min. Nine of the nine patients maintained fistula and vein patency at three months.

TABLE 1

Results from Example 1

| Patient Study (9 patients) | Results |
| --- | --- |
| Successful fistula formation | 100% (9/9) |
| Average time to dialysis readiness | 62 days (n = 9) |
| Fistula/vein patency at three months | 100% (9/9) |

Example 2

A total of seven patients received a percutaneously-formed fistula between a proximal ulnar artery and a deep ulnar vein of an arm of each patient. To form the fistula, a first catheter carrying an electrode was percutaneously positioned in the deep ulnar vein (via cephalic, basilic, or brachial vein access) and a second catheter was percutaneously positioned in the proximal ulnar artery (via brachial artery access), and the electrode ablated tissue between the proximal ulnar artery and the deep ulnar vein to remove tissue between the vessels. The arm was not immobilized during the formation of the fistula. Patient follow-ups occurred at one, two, and three months. During follow-ups, one or more vessels were coil embolized in some patients at the discretion of the physician. Two patients received balloon angioplasty at three months, and one patient received balloon angioplasty and surgical revision at three months.

As shown in Table 2, a fistula was successfully formed in six of seven patients. Of the six patients with a successfully-formed fistula, each maintained fistula and vein patency at three months. One patient was withdrew from the study after the three-month evaluation. Of the remaining five patients, the average time to dialysis readiness was 108 days. Dialysis readiness was determined based on successful initiation of dialysis or physical determination of a flow rate of at least 300 ml/min.

TABLE 2

Results from Example 2

| Patient Study (7 patients) | Results |
| --- | --- |
| Successful fistula formation | 86% (6/7) |
| Average time to dialysis readiness | 108 days (n = 5) |
| Fistula/vein patency at three months following successful fistula formation | 100% (6/6) |

Example 3

A total of eight patients received a percutaneously-formed fistula between a proximal ulnar artery and a deep ulnar vein of an arm of each patient. To form the fistula, a first catheter carrying an electrode was percutaneously positioned in the deep ulnar vein (via brachial vein access) and a second catheter was percutaneously positioned in the proximal ulnar artery (via brachial artery access), and the electrode ablated tissue between the proximal ulnar artery and the deep ulnar vein to remove tissue between the vessels. The arm was immobilized at the wrist during the formation of the fistula. The brachial vein was coil embolized during the procedure. Patient follow-ups occurred at one, two, and three months.

As shown in Table 3, a fistula was successfully formed in all eight patients. One patient died of causes unrelated to the procedure (arrhythmia caused by hyperkalemia) prior to the two-month evaluation. A second patient achieved dialysis readiness, but died of causes unrelated to the procedure (septicemia from diabetic foot ulcer) prior to the three-month evaluation. Of the six patients that received a three-month evaluation, five maintained fistula and vein patency at three months. For the six patients that achieved dialysis readiness, the average time to dialysis readiness was 37 days. Dialysis readiness was determined based on successful initiation of dialysis or physical determination of a flow rate of at least 300 ml/min.

TABLE 3

Results from Example 3

| Patient Study (8 patients) | Results |
| --- | --- |
| Successful fistula formation | 100% (8/8) |
| Average time to dialysis readiness | 37 days (n = 6) |
| Fistula/vein patency at three months | 83% (5/6) |

We claim:

1. A method for treating a patient comprising:
   endovascularly advancing a distal portion of a first catheter against venous blood flow into a first deep ulnar vein, the first deep ulnar vein being substantially parallel to a proximal ulnar artery between a brachial artery and an interosseous artery; and
   forming a first fistula between the proximal ulnar artery and the first deep ulnar vein.

2. The method of claim 1 wherein the first catheter comprises a fistula-forming element, and wherein forming the first fistula between the proximal ulnar artery and the first deep ulnar vein comprises forming the first fistula using the fistula-forming element.

3. The method of claim 2 wherein the fistula-forming element comprises an electrode.

4. The method of claim 3 further comprising moving the electrode away from the first catheter against a vessel wall of the first deep ulnar vein and wherein forming the first fistula between the proximal ulnar artery and the first deep ulnar vein comprises ablating the vessel wall of the first deep ulnar vein and a vessel wall of the proximal ulnar artery.

5. The method of claim 1 further comprising advancing a distal portion of a second catheter into the proximal ulnar artery.

6. The method of claim 5 wherein the first and second catheters each comprise one or more magnets and further comprising aligning the first and second catheters using the one or more magnets of each of the first and second catheters.

7. The method of claim 5 wherein the second catheter comprises a fistula-forming element, and wherein forming the first fistula between the proximal ulnar artery and the first deep ulnar vein comprises forming the first fistula using the fistula-forming element.

8. The method of claim 7 wherein the fistula-forming element comprises an electrode.

9. The method of claim 8 further comprising moving the electrode away from the second catheter against a vessel wall of the proximal ulnar artery, and wherein forming the first fistula between the proximal ulnar artery and the first deep ulnar vein comprises ablating the vessel wall of the proximal ulnar artery and a vessel wall of the first deep ulnar vein.

10. The method of claim 5 wherein endovascularly advancing the distal portion of the second catheter into the proximal ulnar artery comprises endovascularly advancing the distal portion of the second catheter into the proximal ulnar artery from the brachial artery.

11. The method of claim 10 further comprising creating an access site in the brachial artery and advancing the second catheter into the brachial artery through the access site.

12. The method of claim 1 wherein endovascularly advancing the distal portion of the first catheter into the first deep ulnar vein comprises endovascularly advancing the distal portion of the first catheter into the first deep ulnar vein from a median cubital vein.

13. The method of claim 12 further comprising forming an access site in a basilic vein, introducing the distal portion of the first catheter into the basilic vein through the access site, and advancing the distal portion of the first catheter into the median cubital vein through the basilic vein.

14. The method of claim 1 wherein endovascularly advancing the distal portion of the first catheter into the first deep ulnar vein comprises endovascularly advancing the distal portion of the first catheter into the first deep ulnar vein from a median cephalic vein.

15. The method of claim 14 further comprising forming an access site in a cephalic vein, introducing the distal portion of the first catheter into the cephalic vein through the access site, and advancing the distal portion of the first catheter into the median cephalic vein through the cephalic vein.

16. The method of claim 1 wherein endovascularly advancing the distal portion of the first catheter into the first deep ulnar vein comprises endovascularly advancing the distal portion of the first catheter into the first deep ulnar vein from a first brachial vein.

17. The method of claim 16 further comprising forming an access site in the first brachial vein, introducing the distal portion of the first catheter into the first brachial vein through the access site.

18. The method of claim 1 further comprising injecting a radiopaque dye into the proximal ulnar artery.

19. The method of claim 1 further comprising forming a second fistula between the proximal ulnar artery and a second deep ulnar vein.

20. The method of claim 1 further comprising cannulating the cephalic vein or the basilic vein to provide dialysis access.

21. A method of treating a patient comprising:
endovascularly advancing a distal portion of a first catheter against venous blood flow through a portion of a basilic vein, a median cubital vein, and into a first deep ulnar vein, the first deep ulnar vein being substantially parallel to an ulnar artery between a brachial artery and an interosseous artery;
endovascularly advancing a distal portion of a second catheter through a portion of the brachial artery and into the ulnar artery; and
forming a fistula between the first deep ulnar vein and the ulnar artery.

22. A method of treating a patient comprising:
endovascularly advancing a distal portion of a first catheter against venous blood flow through a portion of a cephalic vein, a median cephalic vein, and into a first deep ulnar vein, the first deep ulnar vein being substantially parallel to an ulnar artery between a brachial artery and an interosseous artery;
endovascularly advancing a distal portion of a second catheter through a portion of the brachial artery and into the ulnar artery; and
forming a fistula between the first deep ulnar vein and the ulnar artery.

23. A method of treating a patient comprising:
endovascularly advancing a distal portion of a first catheter against venous blood flow through a portion of a brachial vein and into a first deep ulnar vein, the first deep ulnar vein being substantially parallel to an ulnar artery between a brachial artery and an interosseous artery;
endovascularly advancing a distal portion of a second catheter through a portion of the brachial artery and into the ulnar artery; and
forming a fistula between the first deep ulnar vein and the ulnar artery.

* * * * *